US011642322B2

(12) United States Patent
Vanden Avenne (10) Patent No.: US 11,642,322 B2
(45) Date of Patent: *May 9, 2023

(54) FOOD SUPPLEMENT AND COMPOSITION COMPRISING CHOLINE BUTYRATE SALT AND/OR BUTYRYLCHOLINE

(71) Applicant: ABERGAVENNY NV, Antwerp (BE)

(72) Inventor: Marc Vanden Avenne, Antwerp (BE)

(73) Assignee: ABERGAVENNY NV, Antwerp (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/320,382

(22) Filed: May 14, 2021

(65) Prior Publication Data
US 2021/0267917 A1   Sep. 2, 2021

Related U.S. Application Data

(62) Division of application No. 16/096,914, filed as application No. PCT/IB2017/052366 on Apr. 25, 2017, now Pat. No. 11,007,159.

(30) Foreign Application Priority Data

Apr. 27, 2016 (BE) ................................ 2016/5290
Apr. 27, 2016 (BE) ................................ 2016/5291

(51) Int. Cl.
| | | |
|---|---|---|
| *A61K 31/14* | (2006.01) | |
| *A23K 20/174* | (2016.01) | |
| *A23K 20/105* | (2016.01) | |
| *A23K 20/158* | (2016.01) | |
| *A61K 31/19* | (2006.01) | |
| *A61K 31/221* | (2006.01) | |
| *A23L 33/10* | (2016.01) | |
| *A23L 33/15* | (2016.01) | |
| *A61P 1/00* | (2006.01) | |

(52) U.S. Cl.
CPC ............ *A61K 31/14* (2013.01); *A23K 20/105* (2016.05); *A23K 20/158* (2016.05); *A23K 20/174* (2016.05); *A23L 33/10* (2016.08); *A23L 33/15* (2016.08); *A61K 31/19* (2013.01); *A61K 31/221* (2013.01); *A23V 2002/00* (2013.01); *A23V 2250/304* (2013.01); *A61P 1/00* (2018.01)

(58) Field of Classification Search
CPC ...... A61K 31/14; A61K 31/19; A61K 31/221; A23K 20/105; A23K 20/158; A23K 20/174; A23L 33/15; A23V 2002/00; A23V 2250/304

See application file for complete search history.

(56) References Cited

U.S. PATENT DOCUMENTS

| | | | |
|---|---|---|---|
| 1,957,443 A | 5/1934 | Cline | |
| 4,385,053 A | 5/1983 | Reisberg et al. | |
| 5,922,766 A | 7/1999 | Acosta et al. | |
| 6,498,247 B2 * | 12/2002 | Evans | A61K 31/4415 536/65 |
| 8,021,701 B1 | 9/2011 | Perry | |
| 2005/0214383 A1 | 9/2005 | Bubnis et al. | |
| 2007/0065456 A1 | 3/2007 | Woods | |
| 2017/0182108 A1 | 6/2017 | Nakamura | |

FOREIGN PATENT DOCUMENTS

| | | |
|---|---|---|
| DE | 37 38 649 | 5/1989 |
| EP | 1 354 520 | 10/2003 |
| WO | 97/27762 | 8/1997 |
| WO | 2010/054485 | 5/2010 |
| WO | 2011/061687 | 5/2011 |
| WO | 2012/045045 | 4/2012 |
| WO | 2015/147251 | 10/2015 |
| WO | 2015/165492 | 11/2015 |

OTHER PUBLICATIONS

Klein et al., "Choline carboxylate surfactants: biocompatible and highly soluble in water", Green Chemistry, vol. 10, pp. 433-435 (2008).
Muhammad et al., "Synthesis and Physical Properties of Choline Carboxylate Ionic Liquids", Journal of Chemical & Engineering Data, vol. 57, pp. 2191-2196 (2012).
Rengstl et al., "Biocompatible ionic liquids-thermotropic and lyotropic phase behavior", Department of Physical and Theoretical Chemishy, University of Regensburg, Germany, 2010.
Zeisel et al: "The fetal origins of memory: The role of dietary choline in optimal brain development", Journal of Pediatrics, Mosby-Year Book, St. Louis, MO, US, vol. 149, No. 5, Nov. 1, 2006 (Nov. 1, 2006), pp. S131-S136.
Zhiyong Li et al: "Design of environmentally friendly ionic liquid aqueous two-phase systems for the efficient and high activity extraction of proteins", Green Chemistry, vol. 14, No. 10, Jan. 1, 2012 (Jan. 1, 2012), pp. 2941-2950.
International Search Report dated Apr. 7, 2017 in International (PCT) Application No. PCT/IB2017/052366.
Written Opinion of the International Searching Authority dated Apr. 7, 2017 in International (PCT) Application No. PCT/IB2017/052366.
English translation of WO 2015147251 (Year: 2015).
English translation of DE3738649 (Year: 1989).

(Continued)

*Primary Examiner* — Umamaheswari Ramachandran (74) *Attorney, Agent, or Firm* — Wenderoth, Lind & Ponack, L.L.P.

(57) ABSTRACT

The present Invention relates to the use of choline butyrate or butyrylcholine in food and in particular in the treatment of Intestinal disorders and in the stimulation of the brain development. Furthermore, the invention provides for a food supplement and a pharmaceutical composition comprising choline butyrate or butyrylcholine, The invention also relates to an animal feed comprising choline butyrate or butyrylcholine or said food supplement.

10 Claims, 1 Drawing Sheet

(56) References Cited

OTHER PUBLICATIONS

Chaudhari et al. (Int J of Advances in Pharmacy, Biology and Chemistry, 2012). (Year: 2012).
Pohanka et al. (Biomed Pap Med Fac Univ Palacky Olomouc Czech Repub, 2011, 219-230). (Year: 2011).
Queensland, 2016, https://www.earlyyearscount.earlychildhood.qld.gov.au/age-spaces/timeline-brain-development-birth/). (Year: 2016).
Choline (https://lpi.oregonstate.edu/book/export/html/342, Apr. 27, 2015, p. 1, para. 5). (Year: 2015).
Li et al. (Green Chemistry, 2012,14). (Year: 2012).

* cited by examiner

FOOD SUPPLEMENT AND COMPOSITION COMPRISING CHOLINE BUTYRATE SALT AND/OR BUTYRYLCHOLINE

TECHNICAL DOMAIN

The present invention relates to a composition comprising a salt or ester of choline and butyric acid, namely choline butyrate or butyrylcholine for use in pharmaceutical applications and the use of choline butyrate in the food industry, more in particular as a food supplement in animal feed or for human use.

STATE OF THE ART

Choline and butyric acid are known as part of food supplements. Both the use of choline and the use of butyric acid in food supplements have disadvantages. Choline has a hygroscopic nature and must therefore be stored in a protected atmosphere. Some choline salts are known to be less hygroscopic, for example choline bitartrate. However, the counterions in these salts have no other function, as a result of which the weight efficiency of such a salt is low. A higher weight of such a compound is necessary to obtain a same nutritional effect. In most cases, butyric acid is added to a compound or food supplement under the form of a salt. This because of the volatile characteristics and the strongly unpleasant smell. The unpleasant smell also makes butyric acid rather inappropriate for use in food. Here too, a counterion is necessary that in itself often does not have any other function in a compound or a food supplement. The mass of said counterions can be a significant part of said compound and makes said compound less weight-effective.

Further disadvantages of a high weight fraction of counterions is that transport costs and storage costs are unnecessary high, as two different salt compounds have to be stored. Especially in the case of the choline salt, additional precautions must be taken that the storage takes place under a protective atmosphere, in order to prevent the hygroscopic effect.

Another problem with said counterions is that some of the commonly used counterions can have a negative influence on the health of a consumer. A commonly used counterion is for example the sodium ion, as it has a low atomic mass. However, sodium ions stimulate a user to drink more, to produce more wet faeces and they can increase the blood pressure, which can be related to cardiovascular diseases.

Hence, there is a need for an improved method to add both choline and butyric acid to the food of humans and animals, in which above-said disadvantages are minimal.

WO 2015 165 492 describes choline carboxylates for use as a food supplement, in which the carboxylate comprises 6 to 12 carbon atoms. This is because carboxylates that have a lower number of carbon atoms, deteriorate the flow characteristics of the food supplement.

WO 97/27762 describes the use of butyrylcholine as a tastiness-increasing component in cat food. This is also the only function that butyrylcholine has in said cat food. No health advantages are directly related to the use of butyrylcholine.

Choline butyrate is a known compound, the work of Doris Rengstl for example describes the use of choline butyrate as an ion fluid, and Klein et al., *Green Chem.*, 2008, 10, 433-435, describes choline butyrate as a surfactant.

Up to present, the use of choline butyrate has not yet been described in food.

The present invention aims to find a solution for at least some of the above-mentioned problems, the invention aims amongst other things to provide a nutritional amount of choline and butyrate in a highly weight-effective way, preferably, also part of the hygroscopic characteristics is reduced and still more preferably, the unpleasant smell of both ions is also reduced.

SUMMARY OF THE INVENTION

In a first aspect, the invention provides for a use of a chemical compound, in which the compound is a salt or ester of choline and butyric acid, selected from choline butyrate according to formula (I)

or butyrylcholine according to formula (II)

for use as an additive in food or for use in a pharmaceutical composition.

Choline butyrate is 100% weight-effective, the complete weight is composed of active ingredient.

Butyrylcholine is in itself an active ingredient. Butyrylcholine is a neurotransmitter analogue and easily migrates through the blood-brain barrier. Furthermore, butyrylcholine is a precursor for choline and butyrate, which are both active ingredients. It is thus one product that provides for several ingredients for a consumer.

Both offer one compound that comprises two active ingredients (choline and butyric acid derivative), which is also particularly cost-effective. Thus, there is amongst other things only storage of one product necessary, instead of two. For the food industry, thus only one silo is for example necessary. Both compounds are little hygroscopic, as a result of which storage and transport can be easier. Moreover, the compounds have a less unpleasant smell than choline and butyrate separately. Finally, both compounds have a good solubility as a result of which they can be digested quickly and efficiently through the digestive tract.

In a second aspect, the invention provides for a use of a chemical compound, selected from choline butyrate according to formula (I) and, or butyrylcholine according to formula (II) in which X⁻ represents an anion for improving the general health of a consumer.

In a third aspect, the invention provides for a composition, preferably a food supplement or a pharmaceutical composition comprising choline butyrate according to formula (I) and/or butyrylcholine according to formula (II) in which X⁻ represents an anion.

In a fourth aspect, the invention provides for a cattle feed comprising choline butyrate according to formula (I) and/or butyrylcholine according to formula (II) in which X⁻ represents an anion.

In a fifth aspect, the invention provides for a method for feeding animals comprising the step of adding choline butyrate or butyrylcholine to a feed.

In a sixth aspect, the invention provides for a pharmaceutical composition comprising choline butyrate according to formula (I) and/or butyrylcholine according to formula (II) in which X⁻ represents an anion; or a food supplement, preferably for human use, according to the above-said embodiment of the invention.

DETAILED DESCRIPTION

In a first aspect, the invention provides for a use of a chemical compound comprising choline and a component of butyric acid, in which the chemical compound is an ester or a salt of choline and butyric acid, and in which the chemical compound is selected from
choline butyrate according to formula (I)

(I)

Or
butyrylcholine according to formula II (II)

in which X⁻ represents an anion,
for use as in food or in a pharmaceutical composition.

Choline butyrate according to formula (I) is a salt formed by choline as cation and butyrate, the conjugated base of butane acid or butyric acid as anion. Said two ions form an ion compound. This compound is also known as choline butanoate. Choline butyrate has been described in literature, however for other applications. Analysis methods are consequently known. For example, X-ray diffraction in powder form or in crystalline form, NMR in solid form, infrared spectroscopy in solid form, Raman spectroscopy in solid or mass spectrometry form can be used to demonstrate the presence of choline butyrate according to formula (I). Measurement values, physical and chemical characteristics and spectra that have been described in literature for choline butyrate can be used as a reference during the analysis. In this respect, it is for example referred to Klein et al., *Green Chem.*, 2008, 10, 433-435 and 3. Chem. Eng. Data 2012, 57, 2191-2196. Possible other analysis techniques that occur in said publications, can also be used for demonstrating choline butyrate according to formula (I).

Butyrylcholine according to formula (I) is an ester formed between choline and butane acid or butyric acid, an anion X⁻ is present in the compound as a counterion of the tertiary amine. The UIPAC name is (N,N,N-trimethyl)-2-ammoniumethylbutanoate and it has the CAS number 3922-86-9. HPLC techniques, possibly supplemented with mass spectroscopy, can be used to demonstrate the presence and the amount of butyrylcholine.

Butyrylcholine itself has structural similarities with acetyl choline, a neurotransmitter and is therefore an active ingredient. Consequently, butyrylcholine has a positive effect on the brain development, general cognitive state of a user and the functioning of the nervous system. Furthermore, the ester compound in butyrylcholine is susceptible for hydrolysis, hereby, butyrylcholine is split into a choline ion and a butyrate ion. Salts, bases, hydrolases and esterases, such as acetyl choline esterase and pseudo choline esterase can catalyse this hydrolysis. Both the butyrate ion and the choline ion have a positive effect on the system of a consumer of butyrylcholine. Therefore, choline ions and butyrate ions in itself are also active ingredients. Thus, butyrate ions have a positive effect on amongst other things intestinal disorders and choline ions have an advantageous effect on amongst other things the brain development and brain activity. Because the butyrate is found in an ester compound, the unpleasant smell of butyrate is also absent in the food supplement. The active ingredients choline and butyrate are added as one single compound as a food supplement under the form of butyrylcholine, which can be considered a pro-drug.

Because only one compound has to be added, transported and stored, this offers advantages compared to separate choline and butyrate compounds.

The term "food supplement" refers to a composition that is appropriate for being added to food or that can be consumed as a supplement in itself. Consequently, a food supplement comprises components that are appropriate for being consumed by humans and animals.

Both the butyrate ion and the choline ion have a positive effect on the system of a consumer. Therefore, choline ions and butyrate ions are active ingredients. Thus, butyrate ions have a positive effect on amongst other things intestinal disorders and choline ions have an advantageous effect on amongst other things the brain development and brain activity. By combining both active ingredients (choline and butyric acid) into one single chemical compound in food, either as choline butyrate according to formula I, or as butyrylcholine according to formula II, two active ingredients are added in one single compound to said food. Consequently, only one compound must be transported and stored. Because both ions are added as one single compound to said composition, it is avoided that each ion has to be added as a compound with another different counterion. By adding choline butyrate or butyrylcholine to the composition, these counterions can be excluded from the composition. Choline butyrate and butyrylcholine are 100% weight-effective, because the complete mass can be considered as an active ingredient. This results in a composition that comprises the same amount of active ingredients as a mixture of a choline salt and a butyrate salt, but that is lighter in weight than such mixture.

In this way, the weight of the pharmaceutical composition or the food supplement that has to be consumed, can be kept low. Furthermore, choline butyrate and butyrylcholine are to a lesser degree hygroscopic than most other choline compounds. As a result, there are less requirements as to the storage, the airtight or anhydrous atmosphere is not necessary any more. Furthermore, choline butyrate and butyrylcholine have a less unpleasant smell than choline and butyrate separately, as a result of which they are less appropriate for use in food. An additional advantage is that these compounds have a high solubility as a result of which choline can be digested rapidly by the digestive system.

The use of choline butyrate and/or butyrylcholine avoids that a cation must be added to the food. A cation that is commonly used in the technique is the sodium ion as a counterion for butyrate. In this way, it is avoided that the unnecessary sodium is added to the food. A possible alternative composition would be an equimolar mixture of choline chloride and sodium butyrate. This mixture comprises only 76.7 weight percentage of active ingredients. In order to comprise a same amount of active ingredients as choline butyrate or butyrylcholine, 30% more in weight of this mixture must be used than the weight of choline butyrate or butyrylcholine.

In a preferred embodiment, said choline butyrate or butyrylcholine is used as a food supplement.

In a preferred embodiment, said chemical compounds are appropriate for human consumption.

In a preferred embodiment, said choline butyrate or butyrylcholine is used in animal feed. The food supplement is preferably used for animals and more preferably in aquaculture, such as fish and shrimp culture; pet care, such as food for cats, dogs, guinea pigs, horses, tropical fishes, tropical birds or rabbits; pig production, such as food for sows, boars and porkers; poultry production, such as food for mother animals, laying-hens, meat chickens, guinea fowl, turkey or quails; or ruminant production, such as food for calves, cattle, milk cows, goats or sheep.

In another preferred embodiment, both compounds are used as a food supplement for human use.

In a preferred embodiment, said choline butyrate or butyrylcholine is used as cattle feed for non-ruminants, more preferably for pigs or poultry.

Both compounds are partially decomposed in the paunch, therefore, it is less recommended to feed unprotected choline to ruminants.

In a preferred embodiment, choline butyrate according to formula (I) and/or butyrylcholine according to formula II or a food supplement based on these compounds is used as a daily amount corresponding to 350 to 4500 mg of choline butyrate or butyrylcholine/kg feed, preferably 450 to 4000 mg/kg, more preferably 600 to 3500 mg/kg, still more preferably 800 to 3000 mg/kg, even still more preferably 1100 to 2500 mg/kg and most preferably 1200 to 2000 mg/kg, such as 1500 to 1800 mg/kg.

In a further preferred embodiment, the daily amount will correspond to 350 to 3700 mg of choline butyrate and/or butyrylcholine/kg feed for pigs and poultry, preferably 450 to 3000 mg/kg, more preferably 550 to 2300 mg/kg, still more preferably 650 to 1900 mg/kg, even still more preferably 750 to 1500 mg/kg and most preferably 850 to 1100 mg/kg, such as 950 to 1050 mg/kg.

In an alternative preferred embodiment, choline butyrate according to formula (I) and/or butyrylcholine according to formula II or said food supplement is used as a daily amount corresponding to 700 to 2800 mg of choline butyrate and/or butyrylcholine/kg feed for fishes and shrimps, preferably 800 to 2400 mg/kg, more preferably 900 to 2200 mg/kg, still more preferably 1000 to 2000 mg/kg, even still more preferably 1100 to 1800 mg/kg and most preferably 1200 to 1600 mg/kg, such as 1300 to 1500 mg/kg.

In a still alternative preferred embodiment, choline butyrate according to formula (I) and/or butyrylcholine according to formula II or said food supplement is used as a daily amount corresponding to 2300 to 4500 mg of choline butyrate and/or butyrylcholine/kg feed for pets, preferably 2400 to 4200 mg/kg, more preferably 2500 to 4000 mg/kg, still more preferably 2600 to 3800 mg/kg, even still more preferably 2700 to 3500 mg/kg and most preferably 2800 to 3300 mg/kg, such as 2900 to 3000 mg/kg.

In a preferred embodiment of the use, said food supplement is a food supplement according to an embodiment of the invention as will be described later.

In a second aspect, the invention provides for uses of choline butyrate according to formula (I) and/or butyrylcholine according to formula II for improving the general health of a consumer, that is a human being or an animal.

In a preferred embodiment, choline butyrate according to formula (I) and/or butyrylcholine according to formula II and more preferably the pharmaceutical composition or the food supplement according to the present invention is used for the treatment of intestinal disorders, preferably in food-producing animals and/or pets.

In a preferred embodiment, said treatment of intestinal disorders is the improvement of the intestinal health of humans and animals.

In a preferred embodiment, choline butyrate according to formula (I) and/or butyrylcholine according to formula II and more preferably the pharmaceutical composition or the food supplement according to the present invention is used for the inhibition of the growth of bacteria and/or the reduction of bacterial infections in the intestinal tract.

In an embodiment, choline butyrate according to formula (I) and/or butyrylcholine according to formula II and preferably the pharmaceutical composition or the food supplement according to the invention as described here, is used for the suppression and control of potentially enterogenic pathogens, without however disturbing the pH balance in the gastrointestinal tract. The gastrointestinal tract comprises the stomach, with a pH between 3 and 4, the large intestine, with a pH between 6 and 7 and the small intestine with a pH of about 7. Micro-organisms, such as pathogens as neutral or beneficial micro-organisms are mainly present in the small and large intestine. An optimal balance between these groups of micro-organisms is essential for the health of the animals, and in particular for the prevention of infections of the intestines. Hereby, it is important that each part of the gastrointestinal tracts maintains a correct pH and that the microbial balance is also maintained.

In an embodiment, choline butyrate according to formula (I) and/or butyrylcholine according to formula II and preferably a pharmaceutical composition or a food supplement according to the invention as described here is used for the selective elimination, suppression, regulation of one or more enteropathogens or the positive regulation of non-pathogenic gastrointestinal microflora, selected from the group consisting of filamentous micro-organisms with adhesion structures, gram-negative bacteria, gram-positive bacteria, fungi, yeasts and viruses. Contrary to "beneficial or non-pathogenic microbial flora", "(entero)pathogens" are to be understood as micro-organisms that have a detrimental effect on the host, in particular that cause diseases or disorders. Other forms of detrimental effects are a reduced daily food intake, a reduced daily weight increase, an increased food conversion, and in general a reduced health and well-being.

In a further embodiment, the enteropathogens are selected from the group consisting of the bacterial pathogens of the genera *Brachispira, Vibrio, Escherichia, Salmonella* (such as, without being limited, *Salmonella typhimurium, Salmonella enteritidis* and *Salmonella java*), *Shigella, Klebsiella, Erwinia, Yersinia, Campylobacter* (such as, without being limited, *Campylobacter jejuni, Campylobacter coli, Campy-* lobacter laris, and *Campylobacter upsaliensis*), *Helicobacter, Pseudomonas, Enterococcus* and *Clostridium*; preferably *Brachyspira hyodysenteriae*; fungal and yeast pathogens of the genera *Penicillium, Aspergillus, Fusarium, Cephalosporum, Saccharomyces, Candida, Fungi Imperfecti* and *Hemiascomycetes*; and viral pathogens of the genera Norovirus and Rotavirus.

Choline butyrate according to formula (I) and/or butyrylcholine according to formula II and more preferably the pharmaceutical composition or the food supplement according to the present invention is preferably effective against gram-positive as well as gram-negative bacteria. Choline butyrate according to formula (I) and/or butyrylcholine according to formula II and more preferably the pharmaceutical composition or food supplement according to the present invention is preferably effective for the suppression of species of the genus *Staphylococcus, Salmonella* of *Escherichia* or the positive regulation of non-pathogenic gastrointestinal microflora, so that a healthy and well-balanced intestinal flora is obtained.

In a preferred embodiment, choline butyrate according to formula (I) and/or butyrylcholine according to formula II and more preferably the pharmaceutical composition or the food supplement according to the present invention is used for increasing the feed efficiency.

Choline butyrate according to formula (I) and/or butyrylcholine according to formula II and more preferably the pharmaceutical composition or the food supplement according to the present invention work in different ways. In a first instance, they will suppress (inhibit) or eliminate pathogenic micro-organisms in the gastrointestinal tract, as a result of which the risk of infections is reduced. Hereby, preferably only the enteropathogens will be killed, suppressed and/or removed, while the beneficial or non-pathogenic gastrointestinal microbial flora (such as e.g. *Lactobacillus*) is maintained or even promoted.

In animals, the reduction of microbial activity in the gastrointestinal tract will in a second instance result in a decrease in the feed conversion ratio. The feed conversion ratio is a measure for the efficiency with which an animal can convert a particular food amount or mass into body weight, and can be defined as the amount of consumed food divided by the increase in body weight, over a specific period of time. A decrease in the feed conversion ratio is thus linked to an improved feed efficiency in the animal. In poultry, this will also lead to an improved feed conversion with improved growth efficiency, better egg laying and an increase in meat production.

In a preferred embodiment, choline butyrate according to formula (I) and/or butyrylcholine according to formula II and more preferably the pharmaceutical composition or the food supplement according to the present invention is used for improving the intestinal flora in animals, preferably, the non-pathogenic gastrointestinal bacteria are stimulated as a result of which they suppress the pathogenic gastrointestinal bacteria.

In a preferred embodiment, choline butyrate according to formula (I) and/or butyrylcholine according to formula II and more preferably the pharmaceutical composition or the food supplement according to the present invention is used for the prevention of the adhesion of some pathogenic bacteria to the intestinal wall, more preferably, said bacteria are of the genus *Salmonella*.

In a preferred embodiment, choline butyrate according to formula (I) and/or butyrylcholine according to formula II and more preferably the pharmaceutical composition or the food supplement according to the present invention is used for extending the villi in the small intestine. Longer villi cause the inner surface of the small intestine to be larger, as a result of which nutrients can be digested more efficiently. This will eventually lead to a better feed conversion.

In a preferred embodiment, choline butyrate according to formula (I) and/or butyrylcholine according to formula II and more preferably the pharmaceutical composition or the food supplement according to the present invention is used for improving the immunity, preferably, the adaptive immunity is promoted, so that in case of an infection, a less non-specific immune reaction occurs. In animals, non-specific immune reactions such as inflammation reactions require a lot of energy, increasing the feed conversion.

In a preferred embodiment, choline butyrate according to formula (I) and/or butyrylcholine according to formula II and more preferably the pharmaceutical composition or the food supplement according to the present invention is used for improving the zootechnical performance in animals.

In a preferred embodiment, choline butyrate according to formula (I) and/or butyrylcholine according to formula II and more preferably the pharmaceutical composition or the food supplement according to the present invention is used for improving the growth efficiency in animals and preferably for improving the meat development.

Both choline butyrate and butyrylcholine stimulate the synthesis of phospholipids and therefore play a role in the construction of cell membranes. Choline ions can cross the blood-brain barrier, therefore, the use of the compounds according to the present invention has a positive effect on the brain development and the general cognitive condition of a consumer. Choline butyrate and butyrylcholine are precursors for intracellular signal molecules, which improves the general cognitive condition of a consumer. Choline butyrate and butyrylcholine are in particular precursors for acetyl choline, a neurotransmitter. Furthermore, these compounds are an important source of methyl groups that are required anywhere in the organism for an optimal growth and development.

In a preferred embodiment, choline butyrate according to formula (I) and/or butyrylcholine according to formula (II) and more preferably the pharmaceutical composition or the food supplement according to the present invention is used in the treatment of cognitive disorders.

In a preferred embodiment, choline butyrate according to formula (I) and/or butyrylcholine according to formula (II) and more preferably the pharmaceutical composition or the food supplement according to the present invention is used for the stimulation of the brain development.

In a preferred embodiment, choline butyrate according to formula (I) and/or butyrylcholine according to formula (II) and more preferably the pharmaceutical composition or the food supplement according to the present invention is used for improving the cognitive condition of a consumer.

In a preferred embodiment, choline butyrate according to formula (I) and/or butyrylcholine according to formula (II) and more preferably the pharmaceutical composition or the food supplement according to the present invention is used for improving the muscle development.

In a preferred embodiment, choline butyrate according to formula (I) and/or butyrylcholine according to formula (II) and more preferably the pharmaceutical composition or the food supplement according to the present invention is used for supporting the nervous system.

In a preferred embodiment, choline butyrate according to formula (I) and/or butyrylcholine according to formula (II) and more preferably the pharmaceutical composition or the food supplement according to the present invention is used for the prevention of a fat liver. Both compounds ensure an improved transport of fat and regulate the fat metabolism, and this in particular in the liver.

In a third aspect, the invention provides for a composition, preferably a food supplement or a pharmaceutical composition comprising choline butyrate according to formula (I) and/or butyrylcholine according to formula (II).

In a preferred embodiment of said pharmaceutical composition or said food supplement, the choline that is present in said pharmaceutical composition or said food supplement is for at least 50% derived from choline butyrate and/or butyrylcholine, preferably at least 60%, more preferably at least 70%, still more preferably at least 80%, even still more preferably at least 90% and most preferably at least 95%, such as at least 99% or 100%. This keeps the amount of other choline counterions reduced.

In a preferred embodiment, said pharmaceutical composition or said food supplement comprises at least 50 weight percent of choline butyrate and/or butyrylcholine, preferably at least 60 weight percent, more preferably at least 70 weight percent, still more preferably at least 80 weight percent, even still more preferably at least 90 weight percent and most preferably at least 95 weight percent such as 99 weight percent of 100 weight percent.

This has the advantage that said pharmaceutical composition or food supplement is rich of active ingredients and thus has a high effect on the weight of the pharmaceutical composition or the food supplement.

In a preferred embodiment, the molar ratio of choline ions to butyrate ions is in the range of 0.70 to 1.30, preferably 0.80 to 1.20, more preferably 0.90 to 1.10, still more preferably 0.93 to 1.07, even still more preferably 0.95 to 1.05 and most preferably 0.97 to 1.03 in said pharmaceutical composite or said food supplement. Analysis methods are known to determine this ratio, but this ratio between the two ions is preferably determined by measuring the amount of choline ions by means of ion chromatography and by measuring the amount of butyrate ions by means of an HPLC technique.

As to butyrylcholine, the weight fraction derived from X- ions in said butyrylcholine will in a preferred embodiment be lower than 32 weight percent or X- is an ion with a mass lower than or equal to that of Br-, more preferably lower than 26 weight percent or X- is an ion with a mass lower than or equal to that of hydrogen bicarbonate ion, HCO3-, more preferably lower than 17 weight percent or X- is an ion with a mass lower than or equal to that of Cl-, still more preferably lower than 10 weight percent or X- is an ion with a mass lower than or equal to that of F-.

The advantage of such a pharmaceutical composition or food supplement is that a high amount of the present butyrate and choline ions are derived from choline butyrate and/or butyrylcholine and few ions are added with an undesired or unnecessary counterion. This is advantageous for the weight efficiency of said pharmaceutical composition or said food supplement.

In a preferred embodiment, said pharmaceutical composition or said food supplement comprises one or more formulation additives. Preferably, said formulation additive is chosen from the non-limitative list of flow improvers, anticoagulants, odour-masking additives or preservatives. These additives ensure that the composition can easily be used and can be stored for a longer time.

In a preferred embodiment, flow improvers will be added to said formulation. A flow improver is preferably an additive with a Hausner ratio lower than 1.25, more preferably lower than 1.10, still more preferably lower than 1.00, even still more preferably lower than 0.90 and most preferably lower than 0.80. By improving the flow characteristics, said pharmaceutical composition or said food additive can be mixed with a feed. As a result, the pharmaceutical composition or the food supplement is distributed more homogeneously through the feed.

In a preferred embodiment, said pharmaceutical composition or said food supplement comprises one or more nutritional additives. In a preferred embodiment, the nutritional additives are selected from the group comprising aromas and plant extracts, such as carvacrol and capsaicine. In a further preferred embodiment, the nutritional additives are selected from the group comprising antibiotics, vitamins, carotenoids, trace elements, clay products, probiotics, prebiotics, essential oils, enzymes, fat acids and (in)organic salts. Non-limiting examples of organic acids which can be used in an embodiment of the invention, comprise C1-C12 carboxylic acids, in particular non-substituted carboxylic acids such as formic acid, acetic acid, propionic acid, butyric acid and valeric acid; and/or substituted carboxylic acids such as adipic acid, maleic acid, succinylic acid, citric acid, fumaric acid, tartaric acid, lactic acid, gluconic acid, succinic acid and ascorbinic acid, including cyclic carboxylic acid such as picolinic acid. The organic acids can be one or more substituted or unsubstituted carboxylic acids as well as their mixtures, and also saturated, unsaturated, cyclic and/or aliphatic carboxylic acids or their mixtures, as well as metal complexes and/or their salts, as well as their racemic and/or enantiomeric forms. Non-limiting examples of inorganic salts which can be used in an embodiment of the invention, comprise strong salts in small amounts, such as perchloric acid (hydrogen perchlorate), hydroiodic acid, hydrobromic acid (hydrobromic acid), hydrochloride (hydrochloric acid), sulphuric acid and nitric acid; as well as weak inorganic salts such as phosphoric salt, hydrogen fluoride, hypochlorous acid and nitrous acid.

This has the advantage that the pharmaceutical composition or food supplement can be composed in such way that several nutritional requirements of a final consumer can be met.

In a preferred embodiment, said pharmaceutical composition or said food supplement comprises, next to the choline butyrate and/or butyrylcholine according to the present invention, also other salts of choline and/or butyrate. Possible salts comprise a choline halide, such as choline chloride, choline bitartrate, choline dihydrogen citrate, choline bicarbonate, choline salicylate, an alkali metal butyrate, such as sodium or potassium butyrate or an earth alkali metal butyrate, such as magnesium or calcium butyrate. As a result, the action of the choline as the butyrate in the body is extended, and even increased.

Preferably, the additionally added choline salt and/or said butyrate salt is a salt with an average to poor solubility, that is, a solubility of preferably 0.01 to 0.10 mole/l, more preferably 0.02 to 0.09 mole/l, still more preferably 0.03 to 0.08 mole/l, still even more preferably 0.04 to 0.07 mole/l and most preferably 0.05 to 0.06 mole/l. The presence of an averagely or poorly soluble salt ensures that the solubility equilibrium is shifted and that the averagely to poorly soluble salt dissolves even more slowly. In this way, it can be ensured that at the end of the digestive system, averagely to poorly soluble salt is still present that has not been dissolved so that the active ingredient can be released slowly throughout the digestive system. Preferably, the averagely to poorly soluble salt is calcium butyrate, and a part of the calcium butyrate only dissolves in the large intestine, where the butyrate has a positive effect. In this preferred embodiment, the molar ratio of choline ions to butyrate ions is in the range of 0.40 to 1.70, preferably 0.50 to 1.60, more preferably 0.60 to 1.50, still more preferably 0.7 to 1.40, even still more preferably 0.8 to 1.30 and most preferably 0.90 to 1.20, such as 0.95 to 1.10 in said pharmaceutical composition or said food supplement.

In a preferred embodiment, said pharmaceutical composition or said food supplement is in the form of a powder. This has the advantage that the power can be distributed homogeneously through a meal or food. If the composition or the supplement is administered to animals, it has the advantage that this form can be used when the food is flour.

In a preferred embodiment, said pharmaceutical composition or said food supplement is in a granular form. This has the advantage, during the use of the granular form, that the pharmaceutical composition or the food supplement will not blow up, in this way, an operator mixing the pharmaceutical composition or the food supplement under for example a feed, will not inhale the pharmaceutical composition or the food supplement. It is for an operator easier to work with granules than with a powder. Specific formulation additives can be added to the pharmaceutical composition or the food supplement for obtaining said granular salt, such as a carrier as known in the state of the art, preferably a fat matrix.

In a further preferred embodiment, said granule is provided with a coating, preferably, said coating comprises carbohydrates, proteins or lipids, more preferably, it comprises a lipid selected from the list of fat acids, glyceride esters of fat acids, alkyl esters of fat acids or their mixtures. A coating takes away the odour, prevents that water is absorbed by the granule and improves the formulation characteristics, such as the flow characteristics.

In a further preferred embodiment, the coating represents less than 10 weight percent of the weight of said granule, more preferably less than 5 weight percent, still more preferably less than 4 weight percent and most preferably 2 to 3 weight percent.

In a preferred embodiment, said granules, whether or not provided with a coating, have an average particle size of 0.05 mm to 5.00 mm, more preferably 0.10 mm to 4.00 mm, still more preferably 0.20 mm to 3.00 mm, even still more preferably 0.50 mm to 2.00 mm and most preferably 0.75 mm to 1.00 mm.

In an alternative preferred embodiment, said pharmaceutical composition or said food supplement is in the form of a tablet, still more preferably, specific additives are added that allow to make a tablet and that provide the tablet with the desired mechanic characteristics. A tablet form ensures that said pharmaceutical composition or said food supplement can be dosed in an easy way. Preferably, each tablet comprises the same dose and the daily intake can be administered easily.

In still an alternative preferred embodiment, said pharmaceutical composition or said food supplement is dosed in a capsule of gelule, still more preferably, specific additives have been added for allowing to fill the capsules or gelules, such as with a flow improver. A capsule or a gelule ensures that said pharmaceutical composition or said food supplement can be dosed in an easy way. Preferably, each capsule or gelule comprises the same dose and the daily intake can be administered easily.

In an embodiment, the daily dose for human use can be 50 mg per day, more preferably 100 mg, 150 mg, 200 mg, 300 mg, 400 mg, 500 mg to 1 g per day. In an embodiment, one tablet, capsule or gelule will be a daily dose of 50 mg per day, more preferably it will contain 100 mg, 150 mg, 200 mg, 300 mg, 400 mg, 500 mg to 1 g. In another embodiment, the daily recommended dose will be contained in two or more tablets, capsules or gelules.

In a fourth aspect, the invention provides for a cattle food comprising choline butyrate according to formula (I) and/or butyrylcholine according to formula (II).

This allows to add both choline and butyrate ions in one single compound, without adding any undesired or unnecessary ions to the animal feed. This ensures that the animal feed is energetically and nutritionally weigh efficient.

In a preferred embodiment, said animal feed comprises 350 to 4500 mg of choline butyrate and/or butyrylcholine/kg animal feed, preferably 450 to 4000 mg/kg, more preferably 600 to 3500 mg/kg, still more preferably 800 to 3000 mg/kg, even still more preferably 1100 to 2500 mg/kg and most preferably 1200 to 2000 mg/kg, such as 1500 to 1800 mg/kg.

In a preferred embodiment, said animal feed comprises choline ions and butyrate ions in a molar ratio of 0.70 to 1.30, preferably 0.80 to 1.20, more preferably 0.90 to 1.10, still more preferably 0.93 to 1.07, even still more preferably 0.95 to 1.05 and most preferably 0.97 to 1.03 in said animal feed. Analysis methods are known to determine this ratio, but this ratio between the two ions is preferably determined by measuring the amount of choline ions by means of ion chromatography and by measuring the amount of butyrate ions by means of an HPLC technique.

Such animal feed provides an advantageous ratio of choline with respect to butyrate. Both ions have a positive effect on the system of a consumer. Thus, butyrate ions have a positive effect on amongst other things intestinal disorders and choline ions have an advantageous effect on amongst other things the brain development and brain activity.

In a preferred embodiment, said animal feed comprises a food supplement according to an embodiment of the invention.

In a fifth aspect, the invention provides for a method for feeding animals comprising the step of adding choline butyrate to a feed.

In a preferred embodiment, a daily amount of choline butyrate and/or butyrylcholine is added to a feed of 350 to 4500 mg of choline butyrate and/or butyrylcholine/kg feed, preferably 450 to 4000 mg/kg, more preferably 600 to 3500 mg/kg, still more preferably 800 to 3000 mg/kg, even still more preferably 1100 to 2500 mg/kg and most preferably 1200 to 2000 mg/kg, such as 1500 to 1800 mg/kg.

In a further preferred embodiment, a daily amount of choline butyrate and/or butyrylcholine is added to a feed of 350 to 3700 mg of choline butyrate and/or butyrylcholine/kg feed for pigs and poultry, preferably 450 to 3000 mg/kg, more preferably 550 to 2300 mg/kg, still more preferably 650 to 1900 mg/kg, even still more preferably 750 to 1500 mg/kg and most preferably 850 to 1100 mg/kg, such as 950 to 1050 mg/kg.

In an alternative preferred embodiment, a daily amount of choline butyrate and/or butyrylcholine is added to a feed of 700 to 2800 mg of choline butyrate and/or butyrylcholine/kg feed for fished and shrimps, preferably 800 to 2400 mg/kg, more preferably 900 to 2200 mg/kg, still more preferably 1000 to 2000 mg/kg, even still more preferably 1100 to 1800 mg/kg and most preferably 1200 to 1600 mg/kg, such as 1300 to 1500 mg/kg.

In still an alternative preferred embodiment, a daily amount of choline butyrate and/or butyrylcholine is added to a feed of 2300 to 4500 mg of choline butyrate and/or butyrylcholine/kg feed for pets, preferably 2400 to 42000 mg/kg, more preferably 2500 to 4000 mg/kg, still more preferably 2600 to 3800 mg/kg, even still more preferably 2700 to 3500 mg/kg and most preferably 2800 to 3300 mg/kg, such as 2900 to 3000 mg/kg.

In a sixth aspect, the invention provides for a pharmaceutical composition comprising choline butyrate according to formula (I) and/or butyrylcholine according to formula (II) or a food supplement according to the above-said embodiment of the invention.

In a last aspect, the invention provides for methods for preparing choline butyrate.

In a preferred embodiment, a method for preparing choline butyrate comprises the following steps:
providing a watery choline hydroxide solution;
adding butyric acid to said watery choline hydroxide solution;
dehydrating, preferably drying the obtained reaction mixture.

In an alternative preferred embodiment, a method for preparing choline butyrate comprises the following steps:
providing an amount of choline compound solution;
adding an amount of butyric acid to said solution;
adding an amount of base;
dehydrating the obtained reaction mixture for obtaining a deposit;
making a suspension of the deposit in an organic solvent;
removing the solid phase from said suspension for obtaining a filtrate;
removing said organic solvent from the filtrate.

Preferably, the choline compound is a choline salt, with choline as a cation and preferably a halide as an anion, more preferably fluoride, chloride or bromide, most preferably chloride.

Preferably, the molar amounts of choline chloride and butyric acid are equal, and still more preferably, the molar amount of hydroxide compound is also equal.

Alternatively, the amount of butyric acid is 0.9 to 1.1 equivalents of the amount of choline compound, and the amount of base is 0.9 to 1.1 equivalents of the amount of choline compound.

Preferably, said base is a hydroxide compound, more preferably, an alkali metal hydroxide or an earth alkali metal hydroxide, still more preferably lithium hydroxide, sodium hydroxide, potassium hydroxide, magnesium hydroxide or calcium hydroxide and most preferably sodium hydroxide.

Preferably, said organic solvent is a polar organic solvent, more preferably a solvent with a dipole moment of 1.70 to 5.00, more preferably an aprotic polar organic solvent and most preferably acetonitril.

In an alternative preferred embodiment, a method for preparing choline butyrate comprises the following steps:
neutralizing an amount of trimethylamine with an amount of butyric acid, in which trimethyl ammonium butyrate is formed;
adding an amount of ethylene oxide to said trimethyl ammonium butyrate.

In the following, the invention will be described by means of non-limiting examples illustrating the invention, and not meant to be interpreted as limiting the scope of the invention.

EXAMPLES

Example 1: Synthesis of choline butyrate: Neutralization of a choline hydroxide base with butyric acid Butyric acid is added to a solution of choline hydroxide to obtain a fluid choline butyrate. After drying, a solid choline butyrate is obtained.

Example 2: Synthesis of choline butyrate starting from choline chloride with butyric acid and quenching with sodium hydroxide An equimolar amount of butyric acid is added to a choline chloride solution. Under stirring and cooling down, an equimolar amount of sodium hydroxide is added.

After distillation, the residue is again dissolved in acetonitril and the sodium chloride precipitate is filtered. Evaporation of acetonitril provides choline butyrate.

Example 3: In situ synthesis of choline butyrate via choline with TMA butyrate and ethylene oxide:

Trimethyl amine (TMA) is hereby neutralized with butyric acid to obtain trimethyl ammonium butyrate. Then, this can further react with ethylene oxide to obtain choline butyrate.

Example 4: Synthesis of choline butyrate starting from choline chloride by exchanging ions on a solid phase An amount of choline chloride is brought over an anionic resin. Once the chlorine ions have been picked, the choline is released by using an eluent comprising butyric acid and choline butyrate leaves the resin in solution. Said solution comprising choline butyrate is subsequently evaporated in order to remove the eluent and the excess of butyric acid.

Example 5: Synthesis of choline butyrate starting from choline chloride and potassium ethanolate.

An amount of choline chloride is dissolved in ethanol. Thereto, an equimolar amount of potassium ethanolate is added, so that a deposit comprising potassium chloride is formed. This deposit is filtrated and to the filtrate, butyric acid is added, again in an equimolar amount. The latter mixture is evaporated for removing ethanol and a possible excess of butyric acid.

Example 6: Synthesis of butyrylcholine.

An excess of butyric acid is neutralized with 0.1 M NaOH solution. To this neutralized solution, a solution of chlorocholine chloride in methanol is added. The amount of methanol and water are removed by evaporation. The residue is dissolved in an amount of distilled water and brought onto a cation exchange resin. This resin is subsequently washed with distilled water, before eluting the butyrylcholine with 1 molar of HCl. The eluate is subsequently evaporated for obtaining a crystalline product, after which the crystals are washed with acetone. This results in butyrylcholine with a high purity.

Example 7: Feed composition appropriate for piglets comprising choline butyrate or butyryl choline

| Piglet feed (weight percentage) | |
|---|---|
| Soya meal | 22.00 |
| Barley | 40.00 |
| Wheat | 31.00 |
| Vegetable oil | 2.90 |
| L-Lysine-HCl | 0.40 |
| DL-Methionine | 0.10 |
| L-Threonine | 0.10 |
| Minerals | 3.20 |
| Choline butyrate or butyrylcholine | 0.30 |

Example 8: Influence of the composition according to the present invention on the feed conversion ratio (FCR)

396 days old ROSS® 308 meat chickens were used for this test. The test lasted from the first day of life of the chickens till day 39. 198 chickens form the test group and were fed with a feed comprising 1100 mg of choline butyrate per kilogram feed. 198 other chickens form the control group and were fed with the same feed, however without the choline butyrate. The FCR value for the control group was 1.65; that of the test group was 1.57, which is a decrease of 5%. The uncertainty of the measurement value is lower than 0.05.

In a second test, instead of choline butyrate, butyrylcholine was added to the feed. The design of the test was for the rest similar to the one described above. Here too, a decrease of 5% van the FCR value was determined in the group receiving butyrylcholine with respect to the control group.

The addition of both choline butyrate and butyrylcholine had a positive effect on the feed conversion.

Example 9: Influence of the composition according to the present invention on the length of the villi 20 days old ROSS® 308 meat chickens were used for this test. The test lasted from the first day of life of the chickens till day 39. 10 chickens form the test group and were fed with a feed comprising 1100 mg of choline butyrate per kilogram feed. 10 other chickens form the control group and were fed with the same feed, however without the choline butyrate. The average length of the villi of 5 chickens was measured for each group after 14 days. The villi in the control group were 727 µm in average; that of the test group were 779 µm, which is an increase of 7%. The average length of the villi of 5 chickens was measured for each group after 39 days. The villi in the control group were 1013 µm in average; that of the test group were 1231 µm, which is an increase of 21%. The uncertainty of the measurement value is lower than 0.05. Longer villi offer a larger absorption surface in the intestine and thus increase the possibility of absorbing nutrients. Longer villi are also signs of a healthy small intestine.

In a second test, instead of choline butyrate, butyrylcholine was added to the feed. The design of the test was for the rest similar to the one described above. Here too, an increase of 21% of the length of the villi in the test group was determined compared to the control group.

The addition of both choline butyrate and butyrylcholine had a positive effect on the length of the villi.

Example 10: Influence of the composition according to the present invention on Coccidiose infection 496 days old ROSS® 308 meat chickens were used for this test and were placed in a shed that was infected with coccidiose. The test lasted from the first day of life of the chickens till day 39. 248 chickens form the test group and were fed with a feed comprising 1100 mg of choline butyrate per kilogram feed. 248 other chickens form the control group and were fed with the same feed, however without the choline butyrate. The FCR value for the control group was 2.55; that of the test group was 2.22, which is a decrease of 13%. Moreover, in the choline butyrate supplemented group, more animals died. The uncertainty of the measurement value is lower than 0.05.

In a second, similar design, instead of choline butyrate, butyrylcholine was added to the feed. The results were completely similar to the results obtained for choline butyrate.

The addition of both choline butyrate and butyrylcholine had a positive effect on the treatment for coccidiose.

Example 11: Influence of the composition according to the present invention on histologic parameters 20 days old ROSS® 308 meat chickens were used for this test. The test lasted from the first day of life of the chickens till day 14. 10 chickens form the test group and were fed with a feed comprising 1100 mg of choline butyrate per kilogram feed. 10 other chickens form the control group and were fed with the same feed, however without the choline butyrate. On day 14, the average amount of CD3+ T-cells was determined for both groups. For the control group, the surface percentage for CD3+ was 18, for the test group, the surface percentage for CD3+ was 23, which is an increase of 27%. The CD3+ value is a marker for the mucosal immunity. Mucosal immunity is built in the first 21 days of life.

In a similar design, butyrylcholine was added to the feed. The obtained results were equal to these with choline butyrate: in the test group, an increase of the surface percentage for CD3+ was observed compared to the control group.

Both choline butyrate and butyrylcholine thus increase the immunity in young animals.

Figure 1:
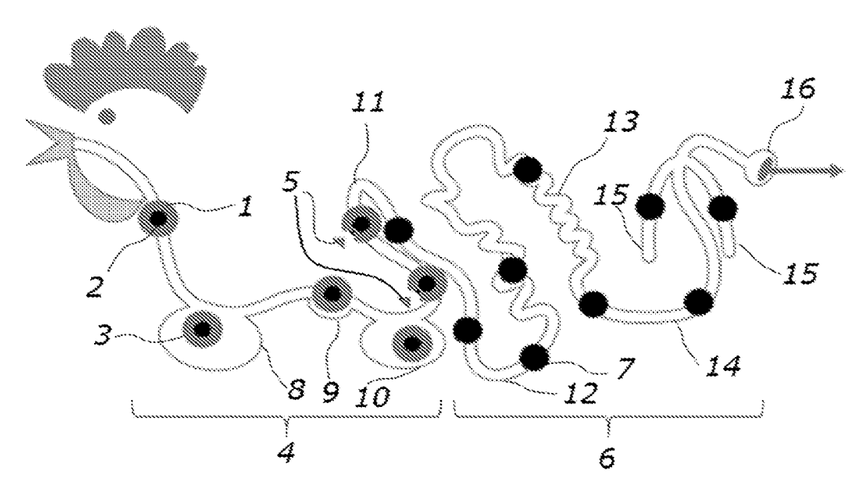
FIG. 1 shows a schematic representation of the digestive tract of a chicken and the action of a coated choline butyrate or butyrylcholine comprising granule.

Example 12:

FIG. 1 shows a schematic representation of the digestive tract of a chicken and the action of a coated choline butyrate or butyrylcholine comprising granule 3. The coated granule comprises a lipid coating 1 and a granule core 2 comprising choline butyrate. This coated granule stays intact when passing through the stomach part 4. The stomach part 4 consists amongst other things of the crop 8, the glandular stomach 9 and the muscular stomach 10. In the duodenum 11, lipases ensure the coating is decomposed 5. The uncoated granule 7 gradually releases its content in the rest of the intestine part 6. The latter comprises amongst other things the jejunum 12, the ileum 13, the large intestine 14 and the blind gut 13 until the cloaca 16.

Example 13: Pharmaceutical preparation

The composition of a tablet appropriate as a pharmaceutical preparation for human use according to the present invention is as follows:

| Ingredients | Amount mg per tablet |
| --- | --- |
| Choline butyrate according to formula I or butyrylcholine according to formula II | 300.00 |
| Microcrystalline cellulose | 230 |
| Magnesium Stearate | 10.0 |
| Silicon dioxide | 10.0 |
| TOTAL | 550 |

The invention claimed is:

1. A method of improving the cognitive condition of a human comprising administering a pharmaceutical composition or food supplemental to the human,
   wherein the pharmaceutical composition or food supplemental comprises choline butyrate according to formula (I):

$$H_3C \smile \overset{O}{\underset{\|}{C}} \smile O^- \left[ \smile \overset{|}{\underset{|}{N^+}} \smile OH \right],$$  (I)

as the only active ingredient, and
   wherein a daily dosage of the choline butyrate according to formula (I) is approximately 300 mg per day.

2. The method according to claim 1, wherein the pharmaceutical composition or food supplemental comprises at least 50% by weight of the choline butyrate according to formula (I).

3. The method according to claim 1,
wherein the pharmaceutical composition or food supplemental is formulated in a tablet, and
wherein the pharmaceutical composition or food supplemental comprises at least 90% by weight of the choline butyrate according to formula (I).

4. The method according to claim 1,
wherein the pharmaceutical composition or food supplemental is formulated in a powder or granular form, a tablet, or a capsule.

5. A method of improving intestinal health in a human and improving the cognitive condition of the human comprising administering a pharmaceutical composition or food supplemental to the human,
wherein the pharmaceutical composition or food supplemental comprises choline butyrate according to formula (I):

as the only active ingredient, and
wherein a daily dosage of the choline butyrate according to formula (I) is 50 mg to 1 g per day.

6. The method according to claim 5, wherein the daily dosage of the choline butyrate according to formula (I) is 100 mg to 1 g per day.

7. The method according to claim 5, wherein the daily dosage of the choline butyrate according to formula (I) is 200 mg to 400 mg per day.

8. The method according to claim 5, wherein the pharmaceutical composition or food supplemental comprises at least 50% by weight of the choline butyrate according to formula (I).

9. The method according to claim 5,
wherein the pharmaceutical composition or food supplemental is formulated in a tablet,
wherein the pharmaceutical composition or food supplemental comprises at least 90% by weight of the choline butyrate according to formula (I), and
wherein the daily dosage of the choline butyrate according to formula (I) is approximately 300 mg per day.

10. The method according to claim 5,
wherein the pharmaceutical composition or food supplemental is formulated in a powder or granular form, a tablet, or a capsule.

* * * * *